Figure 1:
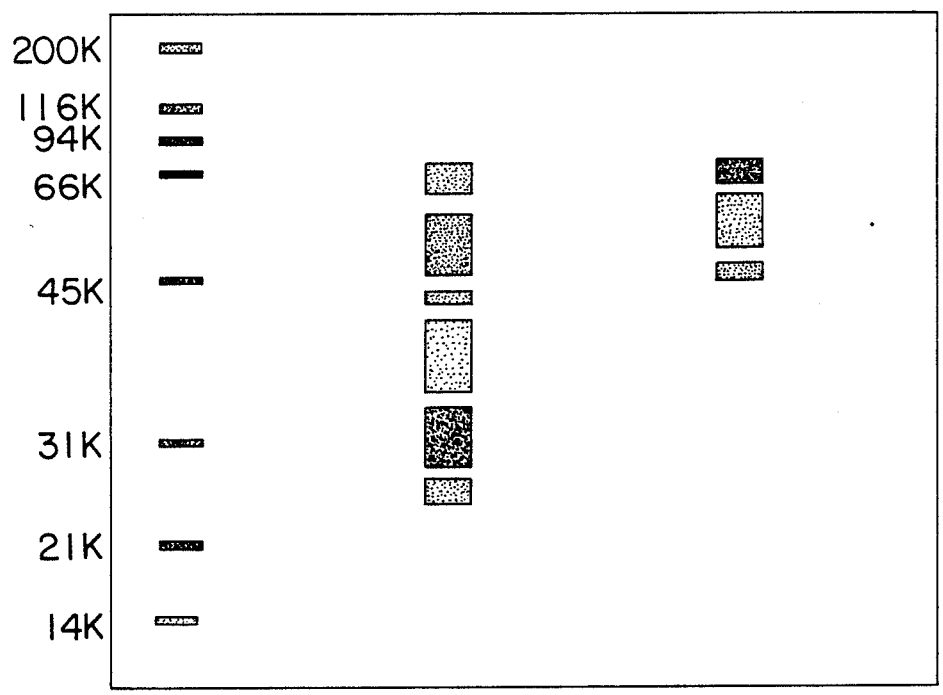

United States Patent [19]

Hinman et al.

[11] Patent Number: 4,956,467

[45] Date of Patent: Sep. 11, 1990

[54] NUCLEOPHILIC TERTIARY ORGANOPHOSPHINES

[75] Inventors: Lois M. Hinman, North Tarrytown; Libby S. Miller, New York City, both of N.Y.

[73] Assignee: American Cyanamid Company, Stamford, Conn.

[21] Appl. No.: 333,803

[22] Filed: Apr. 5, 1989

Related U.S. Application Data

[63] Continuation-in-part of Ser. No. 176,571, Apr. 1, 1988, abandoned.

[51] Int. Cl.$^5$ .................. C07F 9/50; C07F 9/572; C07F 9/58; C07F 9/6506
[52] U.S. Cl. ...................................... 548/112; 544/82; 544/84; 544/124; 544/139; 544/141; 544/157; 546/22; 548/413; 564/15; 568/13
[58] Field of Search .................. 544/157, 82, 84, 124, 544/139, 141; 546/22; 548/112, 413; 564/15; 568/13

[56] References Cited

U.S. PATENT DOCUMENTS 3,754,035  8/1973  Grayson ............................... 564/15

*Primary Examiner*—Richard L. Raymond
*Attorney, Agent, or Firm*—Charles J. Fickey

[57] ABSTRACT

Novel nucleophilic tertiary organophosphines and the specific cleavage of peptide bonds by nucleophilic tertiary organophosphines. This invention is of particular utility in providing chemical agents for use in the cleavage of proteins and the determination of the amino acid sequence of proteins.

7 Claims, 3 Drawing Sheets

FIG. 3
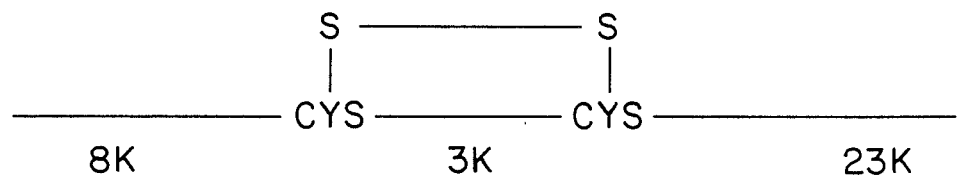
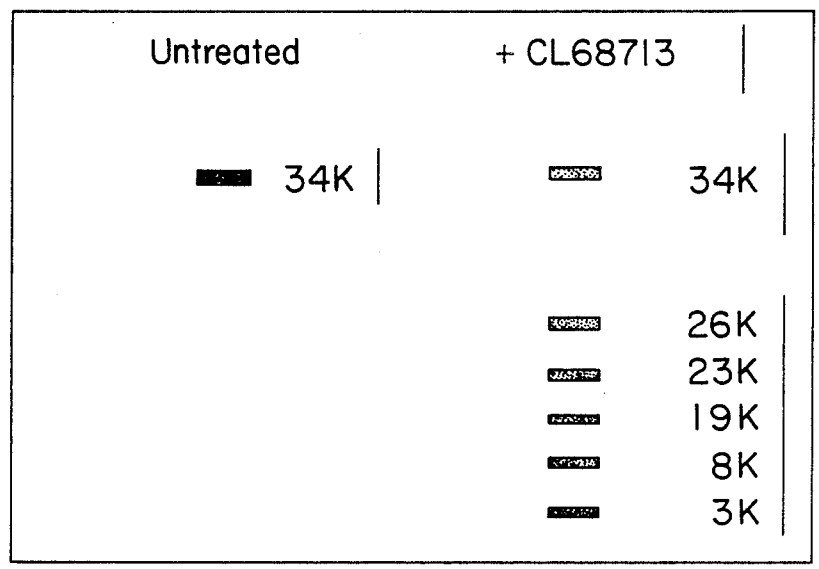

NUCLEOPHILIC TERTIARY ORGANOPHOSPHINES

This application is a continuation-in-part of application Serial No. 071 176,571 filed 1988, now abandoned.

FIELD OF THE INVENTION

The invention relates to novel nucleophilic tertiary organophosphines and the specific cleavage of peptide bonds by nucleophilic tertiary organophosphines. This invention is of particular utility in providing chemical agents for use in the cleavage of proteins and the determination of the amino acid sequence of proteins.

DESCRIPTION OF THE PRIOR ART

Determination of the sequence of amino acids in a protein requires a reproducible method of cleaving polypeptide chains into fragments. A strategy for amino acid sequence analysis requires that a protein be cleaved into fragments by at least two different specific methods so that sequences of overlapping peptide fragments can be obtained.

Various methods for cleaving the polypeptide chains are known, e.g. enzymatic and chemical, which are discussed as follows. The ability of proteolytic enzymes such as trypsin, chymotrypsin, thermolysin and pepsin to cleave proteins at unique sites based upon amino acid sequence is well known to those skilled in the art. Of these enzymes, trypsin is the most specific protease cleaving a polypeptide on the C-terminal side of lysine or arginine residues. Chymotrypsin and pepsin cleave a polypeptide at the C-terminal side of phenylalanine, tryptophan or tyrosine residues while thermolysin cleaves at the N-terminal side of leucine, isoleucine or valine residues. [Lehninger, A. L., *Biochemistry* 2nd edition, 1975, Worth Publishers].

Of the chemical methods for cleaving polypeptide chains, the most common involves the use of cyanogen bromide which cleaves on the C-terminal side of methionine residues. [Gross, E., The cyanogen bromide reaction, *Methods in Enzymology*, 11, 238, 1967]. Other chemical cleavage reactions include cleavage at tryptophanyl residues by N-bromosuccinimide [Schecter, Y., Patchornik, A. and Burstein, Y, Selective chemical cleavage of tryptophanyl peptide bonds by oxidative chlorination with N-bromosuccinimide, *Biochemistry*, 11 5071, 1976]. This reaction tends to be relatively inefficient in proteins, cleaving only 10 to 50% of the tryptophanyl peptide bonds in proteins. Additional chemical cleavage agents which react primarily at tryptophanyl residues have been described. These include 2-(2-nitrophenyl-sulfonyl)-3-methyl-3-bromo -indolenine [Fontana, A., Modification of Tryptohan with BNPS-skatole, *Meth. Enzymology*, 25, 29, 1972], 2,4,6-tribromo-4-methyl-cyclohexadione [Burstein Y. and Patchornik, A., Selective chemical cleavage of tryptophanyl peptide bonds in peptides and proteins, *Biochemistry*, 11, 4641, 1972], o-iodobenzoic acid [Mahoney, W. C. and Hermodson, M. A., High yield of cleavage of tryptophanyl peptide bonds by o-iodobenzoic acid, *Biochemistry*, 8, 3810, 1979] and N-chlorosuccinimide [Schecter, Y., Patchornik, A. and Burstein, Y., Selective chemical cleavage of tryptophanyl peptide bonds by oxidative chlorination with N-chlorosuccinimide, *Biochemistry*, 15, 5071, 1976]. As with the N-bromosuccinimide reaction, all of these agents result in relatively inefficient cleavage and further result in the chemical modification of some other amino acid residues. Furthermore, hydroxylamine is known to cleave polypeptides at asparaginyl-glycyl peptide bonds [Bornstein, P. and Balian, G., Cleavage of Asn-Gly bonds with hydroxylamine, *Meth. Enzymology*, 47, 132, 1977]. All of these cleavage methods work optimally only on reduced and alkylated proteins rather than on proteins with intact disulfide bonds.

It is also known that cleavage of polypeptides at cysteine or serine can be accomplished by conversion of the amino acid residue to dehydroalanine and subsequent hydrolysis of the dehydroalaninecontaining polypeptide in acid. [Witkop, B. and Ramachandran, L. K. Progress in nonenzymatic selective modification and cleavage of proteins, *Metabolism*, 13, 1016, 1064; Patchornik, A. and Sokolooslky, M., Nonenzymatic cleavages of peptide chains at cystine and serine residues through their conversion into dehydroalanine residues, *J. Amer. Chem. Soc.*, 86, 1206, 1964; Sokoloosky, M. Sadeh, T. and Patchornik, A., Nonenzymatic cleavage of peptide chains at the cystine and serine residues through their conversion to dehydroalanine (DHAL). II. The specific chemical cleavage of cysteinyl peptides, *J. Amer. Chem. Soc.*, 86, 1212, 1964]The only chemical agent known prior to the invention herein described which would uniquely cleave a polypeptide at cystine residues is cyanide. [Cartsimpoolas, N. and Wood, J. L. The reaction of cyanide with bovine serum albumin, *J. Biol. Chem.*, 4132, 1964; Cartsimpoolas, N. and Wood, J. L., Specific cleavage of cystine peptides by cyanide, *J. Biol. Chem.*, 241, 1790, 1966]Cyanide reacts with cystine to yield a sulfhydryl group and a thiocyano group. The thiocyano-containing derivative will cyclize at a pH of 8 or below and then undergo hydrolysis to cleave the peptide bond. Cleavage at cysteine or cystine residues can be accomplished by reacting a polypeptide with 2-nitro-5-thiocyano-benzoic acid. [Jacobson, G. R., Schaffer, M. H., Stank, G. R., Vanaman, T. C., Specific chemical cleavage in high yield at the amino peptide bonds of cysteine and cystine residues. *J. Biol. Chem.*, 248, 6583, 1973]. The N-terminus of the polypeptide is blocked by this method and requires additional treatment with a nickel and sodium borohydride catalyst to convert the modified amino acid residue to alanine. Cleavage of phenylalanyl -seryl and phenylalanylthreonyl peptide bonds by cyanide and cyano-derivatives has also been reported (Witkop, B and Ramachandran, L. K., Progress in Nonenzymatic Selective Modification and Cleavage of Proteins, Metabolism, 13 1016,1064). However, because of a lack of specificity in the cleavage reaction and concomittant modifications of other amino acid residues by cyanide, this reaction is only rarely used as a cleavage method in protein chemistry.

Certain tertiary organophosphines have been described as having the ability to alter the configuration of keratin fibers and, under certain conditions, cause depilation of hair. U.S. Patent No. 3,489,811 to Drucker et al. discloses certain tertiary organic phosphines which are suitable for cosmetic uses such as in hair-waving compositions. In addition, that patent discloses and claims processes for producing a substantially odor-free tertiary phosphine. The use of particular organic phosphines to deform keratin fibers or cause depilation is disclosed in U.S. Pat. No. 3,628,910 to Grayson. The Grayson patent teaches that the deformation and depilation effects on keratin fibers by particular organic phosphines are the result of the rupture and reformation of cystine disulfide bond linkages which exist between polypeptides of keratin fibers. Furthermore, the ability of certain unsymmetrical tertiary organophosphines to effect depilation is disclosed in U.S. Patent No. 3,754,035 to Grayson. Here, too, it is taught that the effect of such organophosphines is to cleave disulfide bonds of the hair keratin. The ability for organic phosphines to reduce disulfide bonds by acting as reducing agents has been shown using model compounds. In addition, the use of tributylphosphine as a reducing agent in protein research has been reported. [Ruegg, U. T. and Rudingo, J. Reductive Cleavage of Cystine Disulfides with Tributylphosphine, Methods in Enzymology, 47, 111-126]. However, as far as we are aware, until the present invention, it was not know that nucleophilic tertiary organophosphines would effect specific peptide bond cleavage.

Therefore, it is a primary object of this invention to provide nucleophilic tertiary organophosphines which are capable of effecting peptide bond cleavage. It is a further specific object of this invention to provide nucleophilic tertiary organophosphines which are capable of effecting peptide bond cleavage in a specific manner. Still further, it is an object of this invention to provide methods to be used with such nucleophilic tertiary organophosphines to effect such peptide bond cleavage. Additional objects and advantages of the present invention will be set forth in part in the description which follows and in part will be obvious from the description or may be learned by practice of the invention as hereinafter described and claimed.

SUMMARY OF THE INVENTION

The novel nucleophillic tertiary organophosphines of the present invention can be represented by the formula:

$$Q-\underset{\underset{Q''}{|}}{P}-Q'$$

Wherein Q is $-(CH_2)_n-CH\underset{R_5}{|}-\underset{\underset{R_4}{|}}{C}-Z$;

Q' is Q or Q''

Q'' is $-(CH_2)_m-CH\underset{R_6}{|}-\underset{\underset{R_8}{|}}{C}-Y$;

Y and Z are, $-NR_{10}R_{11}$ or $-OR_{12}$;
$R_{10}$ and $R_{11}$ taken with the N form imidazolyl, pyrolidonyl, pyridyl or morpholinyl rings;

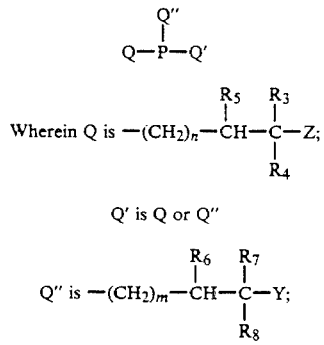

$R_{13}$ is $[CH(R_{17})]_t$—OH  $R_{16}$ and $R_{17}$ are independently —H or —OH
n,m and t are independently 0-3; $R_3$, $R_4$, $R_5$, $R_6$, $R_7$, $R_8$, $R_{14}$ and $R_{15}$ are independently H or alkyl ($C_1-C_4$); with the provisos that: Z and Y are not the same for any given compound.

In addition to the foregoing novel nucleophilic tertiary organophosphines present invention is also directed to the novel use of nucleophilic tertiary organophosphines as specific peptide bond cleavage agents. The nucleophilic tertiary organophosphines used in this invention to specifically cleave peptide bonds at cysteine as hereinafter described can be represented by the formula:

$$Q-\underset{\underset{Q''}{|}}{P}-Q'$$

Wherein Q is $-(CH_2)_n-CH\underset{R_5}{|}-\underset{\underset{R_4}{|}}{C}-Z$;

Q' is Q or Q''

Q'' is $-(CH_2)_m-CH\underset{R_6}{|}-\underset{\underset{R_8}{|}}{C}-Y$;

Y and Z are —OH, $-NR_{10}R_{11}$ or $-OR_{12}$;
$R_{10}$ and $R_{11}$ are independently H or alkyl ($C_1-C_4$); or
$R_{10}$ and $R_{11}$ taken with N form morpholinyl, piperidinyl, imidazolyl or pyrrolidinyl; or
$R_{11}$ is acetyl, carbamyl or guanyl when $R_{10}$ is H;

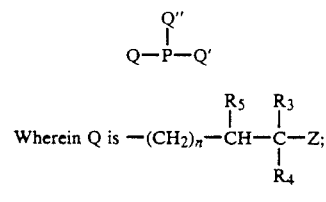

$R_{13}$ is $-[CH_2(R_{17})]_t$—OH;
$R_{16}$ and $R_{17}$ are independently —H or —OH;
$R_{14}$ and $R_{15}$ are indepenly —H or alkyl ($C_1-C_4$);

DETAILED DESCRIPTION OF THE INVENTION PREPARATION OF NUCLEOPHILIC TERTIARY ORGANOPHOSPHINE

The nucleophilic tertiary organophosphines of the present invention are prepared by procedures well known to those skilled in art. See, for example, J. Org. Chem. 26, 5138 (1961); U.S. Pat. No. 2,803,597 to Stiles, et al; and U.S. Pat. No. 3,754,036 to Grayson. A. The following Examples will serve to illustrate the invention in more detail and should not be construed to limit the scope of the invention in any way. The general procedure is to react phosphine ($PH_3$) in a pressurized vessel with a terminally ethylenic unsaturated amine or alcohol in the presence of a free radical initiator such as 2,2' azobis(2-methylbutyronitrile) (hereinafter sometimes referred to as ABN). After separation of the desired product (primary or secondary phosphine) from the reaction mixture by distillation, it is dissolved in a suitable solvent and reacted in an inert atmosphere with a terminally ethylenically unsaturated alcohol or amine, again in the presence of a free radical initiator. Typical of the terminally ethylenic unsaturated amines are 3-allyl-1-p-morpholine, 3-allyl-1-imidazole, 3-allyl-1-pyrrollidone and 3-N,N-diethylaminopropropene. Typical of the terminally ethylenic alcohols are 3-hydroxypropene, ally-2-hydroxyethyl ether and 6,7-dihydroxy-4-oxahept-1-ene (3-allyloxy-1,2-propane-diol).

Whether Q is the same as Q'' in the formula:

is dependent on the reaction ratios used in the above described reactions. Product purity of the compounds produced according to the above process can be established by microanalysis and $^{31}P$ NMR spectroscopy.

EXAMPLE 1

A. 3-N,N-Diethylaminopropylphosphine

A one gallon autoclave containing 500ml. 2-propanol was pressurized to 600 psi with $PH_3$ and heated to 85° C. A mixture of 500g (4.4 moles) N,N-diethylallylamine, 500g 2-propanol and 10g (0.05 moles) 2,2'-azobis(2-methylbutyronitrile) was fed into the system to a total charge of 1500g. The reaction was maintained at 600 psi for 2 hours and then heated at 85° for 1 hour. The autoclave was vented and the primary phoshine (229g, 1 54 moles) was separated from the solvent and secondary & tertiary phosphine products by distillation.

B. 3-Diethylaminopropyl bis (3-imidazolyl propyl)phosphine 18.5g of 3-N,N-diethylaminopropylphosphine from part A above was dissolved in 150ml of 2-propanol in a reaction flask containing an inert atmosphere. One-half gram 2,2'-azobis(2-methylbutyronitrile) was added to the solution which was then heated in an oil bath to 55-60° C. A solution of 28.1 g of allylimidazole in 30ml of 2-propanol was added dropwise to the reaction mixture over a period of 45 minutes keeping the temperature of the reaction mixture between 55-60° C. The reaction mixture was then heated to 75° C for 6 hours. Then, the solvent, starting materials and intermediates were stripped off under high vacuum. The product (27g),3-diethylaminopropylbis(3-imidazolylpropyl)-phosphine, remained in the distillation pot at 200° C. and 0.1 mm Hg. Further purification of the product, if desired, could be accomplished by distillation using a bulb-to-bulb apparatus (e.g., Kugelrohr) at 200° C. and 0.1mm Hg.

EXAMPLE 2

3-Diethylaminoproylbis(2-hydroxyethyloxy-3-propyl)-phosohine 14.2g of 3-N,N-diethylaminopropylphosphine (prepared as described in Example 1, Part A above) was dissolved in 150 ml of 2-propanol in a reaction flask containing an inert atmosphere. Onehalf gram 2,2'-azobis(2-methylbutyronitrile) was added to the solution and the solution was heated to 70° C. A solution containing 22.4g of allylhydroxyethylether in 50ml of 2-propanol was added dropwise to the reaction mixture over a 45 minute period while maintaining the temperature of the reaction mixture between 70-80 The temperature of the reaction mixture was then maintained at 70-80° C. for an additional 6 hours with the addition of 0.5g of ABN at 3.5 hours. The product, 21g of 3-diethylaminopropyl-bis(2-hydroxy-ethyloxy-3propyl)-phosphine, was separated from the solvent, starting materials and intermediates and purified as described in Example 1.

EXAMPLES 3,4 and 5

The tertiary phosphines listed in Table 1 were prepared from the respective aminoalkyl or cycloaminoalkyl phosphine intermediates and alkenols using the process described in Example 1.

EXAMPLE 6

A. 3-Hydroxyoroyvlohosohine

3-Hydroxypropy(phosphine was prepared from $PH_3$ and allyl alcohol in the presence of 2,2'-azobis(2-methylsobutyronitrile) essentially as in Example 1A.

B. 3-Hydroxyprooyl bis(3-imidazolylyroovl) phosohine (6) (mixture with #5, above).

12.0g of the reaction product of Part A, above, was dissolved in 150ml of 2-propanol in a reaction flask under an inert atmosphere. Then, 0.5g of ABN was added and the mixture was heated to 50-55° C. A mixture containing 28.g of 3-allylimidazole in 30ml of 2-propanol was added dropwise to the reaction mixture over a 30 minute period. The reaction mixture was then heated at 80° C. for a total of 6 hours with the addition of 0.2g ABN at 3 hours. The reaction produced an inseparable mixture of 20% 3-imidazolylpropylbis (3-hydroxy-propyl)phosphine (5) and 80% 3-hydroxy-propylbis(3-imidazolylpropyl)phosphine (6) which were separated from the starting material, intermediates and solvent essentially as described in Example 1.

TABLE 1

| Example | Phosphine Intermediate | Alkenol |
|---|---|---|
| 3 | $(C_2H_5)_2N-(CH_2)_3-PH_2$ | $H_2C=CH-CH_2-O-CH_2-CH(OH)-CH_2OH$ |
| 4 | 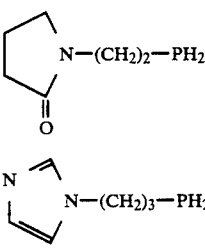 | $H_2C=CH-CH_2-O-CH_2-CH(OH)-CH_2OH$ |
| 5 | 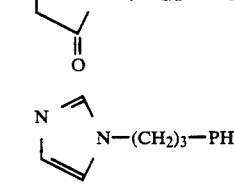 | $H_2C=CH_2-CH_2-OH$ |

| Example | Tertiary Phosphine Product |
|---|---|
| 3 | $(C_2H_5)_2N-(CH_2)_3-P-[(CH_2)_3-O-CH_2-CH(OH)-CH_2OH]_2$ |

TABLE 1-continued

4: N—(CH$_2$)$_2$—P—[(CH$_2$)$_3$—O—CH$_2$—CH(OH)—CH$_2$OH]$_2$ (pyrrolidinone ring with N, C=O)

5: N—(CH$_2$)$_3$—P—(CH$_2$—CH$_2$—CH$_2$—OH)$_2$ (imidazole ring attached via N)

TABLE 2

| Example | Tertiary Phosphine Product | Theory C | Theory H | Theory N | Theory P | Found C | Found H | Found N | Found P |
|---|---|---|---|---|---|---|---|---|---|
| 1 | (C$_2$H$_5$)$_2$N—(CH$_2$)$_3$—P[(CH$_2$)$_3$N(imidazole)]$_2$ | 59.82 | 9.52 | 18.35 | 8.12 | 60.85 | 9.60 | 18.71 | 8.00 |
| 2 | (C$_2$H$_5$)$_2$N—(CH$_2$)$_3$—P—[(CH$_2$)$_3$—O—CH$_2$CH$_2$OH]$_2$ | 58.07 | 10.90 | 3.99 | 8.57 | 57.80 | 10.22 | 3.88 | 8.63 |
| 3 | (C$_2$H$_5$)$_2$N—(CH$_2$)$_3$—P[(CH$_2$)$_3$—O—CH$_2$—CH(OH)—CH$_2$OH]$_2$ | 55.45 | 10.29 | 3.40 | 7.50 | 55.39 | 10.14 | 3.33 | 7.15 |
| 4 | (pyrrolidinone)N(CH$_2$)$_2$—P[(CH$_2$)$_3$—O—CH$_2$—CH(OH)—CH$_2$OH]$_2$ | 52.81 | 8.86 | 3.42 | 7.56 | 52.64 | 9.01 | 2.78 | 6.08 |
| 5 | (imidazole)N—(CH$_2$)$_3$—P[(CH$_2$)$_2$CH$_2$OH]$_2$ | 55.81 | 8.96 | 10.25 | 11.99 | 55.82 | 8.67 | 12.15 | 10.75 |
| 6 | HOCH$_2$—(CH$_2$)$_2$—P[(CH$_2$)$_3$—N(imidazole)]$_2$ (80/20 mixture w/5) | 58.43 | 8.17 | 18.17 | 10.04 | 58.16 | 7.77 | 18.05 | 9.70 |

The reaction products of Example 1-6 were verified by elemental analysis and 31PNMR and the results are listed in Table 2.

Cleavage of Peptide Bonds by Nucleophilic Tertiary Organo Phosphines

Cleavage of peptide bonds in proteins by tertiary organophosphines was studied by treatment of proteins at concentrations ranging from about 0.1 to 5 mg/ml and in a pH range of about 3.0 to 11.0. The results of digestion of the proteins were determined by sodium dodecyl sulfate polyacrylamide gel electrophoresis (SDS-PAGE) according to methods well known to those skilled in that art.

For example, such methods are described by Weber, K. and Osborne, M., The Proteins, H. Neurath and R. L. Hill, editors, Academic Press, New York 19 75, Vol. I 3rd Ed., pp 179-223. The protein bands were identified by staining using either Coomassie Blue-R or Gel-Code silver stain. Specific examples of such cleavage are shown in the following examples which will serve to illustrate the invention in more detail and should not be construed to limit the scope of the invention in any way.

EXAMPLE 7

Cleavage of hair keratin by N,N-diethylamiopropyl-bis-hydroxypropyl)Phosphine

The breakdown of hair keratin by N,N-diethylaminopropyl-bis(3-hydroxypropyl)phosphine as compared with thioglycolate was studied. 200mg of chopped human hair was digested at pH 10.5, 37° C. for 4 hours in 10 ml of 8M urea containing 0.2M N,N-diethylaminopropylbis(3-hydroxypropyl)phosphine or 0.2M sodium thioglycolate. Following digestion, the hair proteins were acetylated by reaction with iodoacetic acid according to the procedure described by Shecter, et al., [J. Invest. Derm. 52 ,57 (1969)]. Samples of the digestion products were then analyzed by SDS-PAGE according to the procedure discussed above. FIG. 1 is a representation of such a gel comparing the digestion of hair by N, N-diethylaminopropylbis(3-hydroxypropyl)phosphine and by sodium thioglycolate. As is shown in FIG. 1, digestion of hair by N,N-diethylaminopropylbis(3-hydroxypropyl)phosphine produces lower molecular weight fragments than those produced by reduction of disulfide bonds alone (i.e., digestion by thioglycolate).

EXAMPLE 8

Cleavage of Bovine Serum Albumin (BSA) by N,N-diethylaminopropylbis(3-hydroxypropyl)phosphine The ability of N, N-diethylaminopropylbis(3-hydroxypropyl)phosphine to cleave BSA was studied and compared with effects of the disulfide bond reducing agents thioglycolate (TG) and 2-mercaptoethanol (EtSH) on BSA. Solutions of BSA at 10mg/ml in 0.1M tris buffer at pH 8.0 were combined with equal volumes of 0.2M N,N-diethylaminopropylbis(3-hydroxypropyl)phosphine, sodium thioglycolate or 2-mercaptoethanol, boiled for 15 minutes and then mixed 1:1 with SDS sample buffer without reducing agent.

Figure 2:
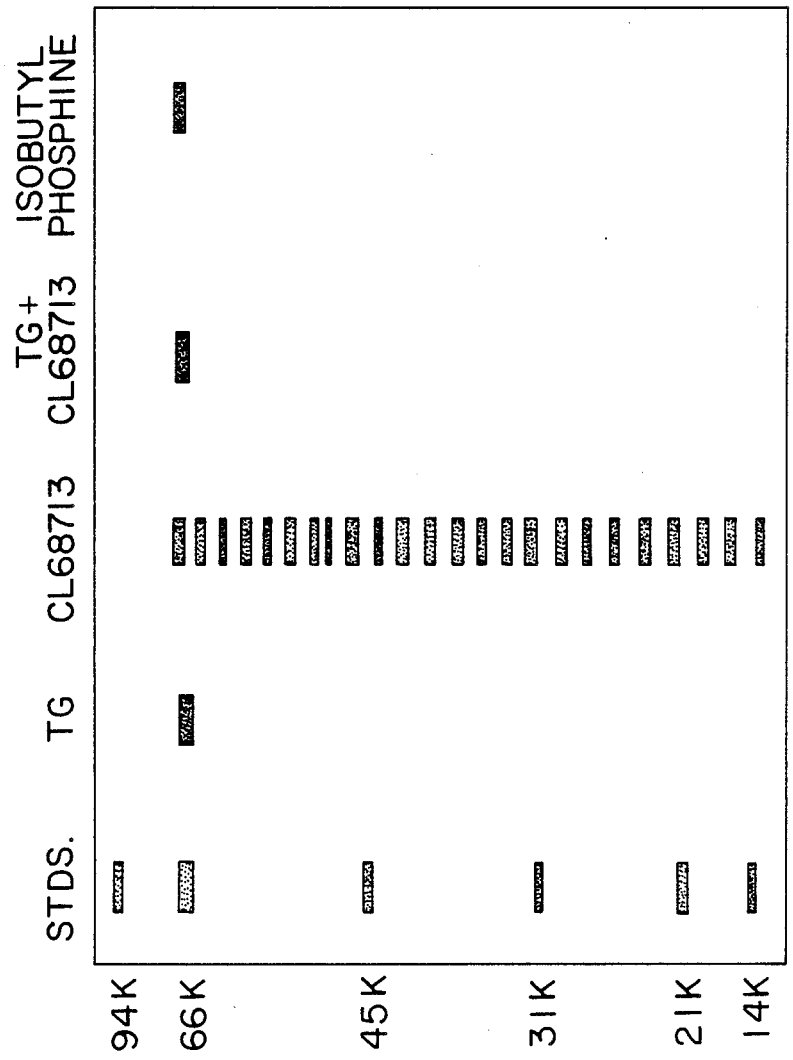

FIG. 2 is a representation of a SDS-PAGE gel showing BSA treated with thioglycolate and BSA treated with N,N-diethylaminopropylbis(3-hydroxy propyl)phosphine. Treatment of BSA with EtSH or TG results in the production of a 66K monomer. Treatment of BSA with N,N-diethylaminopropyl-bis(3-hydroxypropyl)-phosphine results in cleavage of the 66K monomer into smaller peptide fragments indicating disruption of covalent bonds. There is no cleavage of covalent bonds in the 66K monomer by either EtSH or TG.

EXAMPLE 9

Cleavage of Disulfide Bond Reduced Bovine Serum Albumin (BSA) by N,N-diethylaminopropyl-bis (3-hydroxypropyl)phosphine.

The effect of prior reduction of disulfide bonds in BSA upon subsequent cleavage by N,N-diethylaminopropylbis(3-hydroxypropyl)phosphine was studied. A 10 mg/ml sample of BSA was mixed with an equal volume of 0.2M 2-mercaptoethanol or thioglycolate and heated in boiling water for 15 minutes. The reaction mixtures were made 0.2M in N,N-diethylaminopropylbis(3-hydroxypropyl)phosphine and the reaction mixture treated as Example 8.

The results of this study are shown in FIG. 2 which is a representation in a SDS-PAGE gel. As shown in FIG. 2, no peptide bond cleavage by N,N-diethylaminopropylbis-(3-hydroxypropyl)phosphine is observed when the BSA is pretreated with thioglycolate. These results indicate that intact disulfide bonds are required to effect cleavage of proteins by the compounds of this invention.

EXAMPLE 10

Treatment of Sperm Whale Myoglobin with N, N-diethylaminopropylbis(3-hydroxypropyl)phosphine The ability of N,N-diethylaminopropylbis (3-hydroxypropyl)phosphine to cleave sperm whale myoglobin was studied. Sperm whale myoglobin does not contain any cysteine residues. Specifically, the protein was treated at a concentration 10 mg/ml with 0.2m mercaptoethanol or phosphine as in Example 8.

SDS-PAGE showed that sperm whale myoglobin was not cleaved by N,N-diethylaminopropylbis-(3-hydroxy -propyl)phosphine.

EXAMPLE 11

Cleavage of other Cystine Containing Proteins

Using the same procedure as in Example 8, the following proteins, all containing cystine residues, were treated with N,N-diethylaminopropylbis(3-hydroxypropyl)phosphine solutions and the products analyzed by SDS-PAGE: alcohol dehydrogenase, phosphorylase B, pyruvate kinase, creatinine kinase and phosphoglucomutase. All the above proteins showed peptide bond cleavage as evidenced by the presence of lower molecular weight peptide fragments on the SDS gel.

EXAMPLE 12

Determination of Site of Cleavage of Asparaginase by N,N-diethylaminophopylbis(3-hydroxypropyl) phosphine.

To confirm that the primary site of peptide bond cleavage is at cystine residues, purified asparaginase was used as a model protein. The intact polypeptide chain of asparaginase has a molecular weight of 34,000. Cysteine residues occur at residue 76 and 105 in the chain of 321 amino acids. FIG. 3 is a representation of the asparaginase structure and the SDS gel after reaction of asparaginase with N-N-diethylaminopropyl-bis(3-hydroxypropyl)phosphine. The sizes of the peptide fragments were determined from a standard curve plot. The peptide fragments seen after reaction correspond to molecular weights of 26,500, 23,500, 19,000 and 8,000 daltons. In addition, a low molecular weight band (approximately 3000 daltons) is seen. The reaction does not go to completion and considerable parent polypeptide (34K) remains uncleaved.

If the phosphine cleaves all the possible cysteine sites simultaneously, the expected fragments from the primary sequence are 2971, 8055, 11,026, and 23,054 daltons. This obviously is not the case since we see a 26,500 fragment present in the gel pattern. Thus a partial cleavage of the polypeptide occurs as well.

Partial cleavage of the asparaginase with a hit on a single cysteine residue results in the following possible fragments, stating from the amino- terminal end: 8055, 26,025, 11,026, and 23,054. This still does not account for the lack of the 11,025 fragment and the presence of the 19,000 molecular weight band. Therefore, a possible explanation may be advanced as follows: the 11,025 if crosslinked with the 8055 fragment will give a 19,000 fragment. Assuming that the reaction occurs to completion there would remain the 8055 from the simultaneous hit of both cysteine residues but no remaining 11,025 since they are bound up by the excess 8055 fragment. This is consistent with the gel data since a 8055 fragment is visible in the gel.

It appears from the band intensity that the 23,054 fragment is present in approximately twice the concentration of the other fragments. This is likely if the assumption is valid that the two single and simultaneous hits occurs in equal proportions.

EXAMPLE 13

Peptide Bond Cleavage Ability of Other Tertiary Organophosphines

The ability of tertiary organophosphines with and without nucleophilic side-chains to cleave peptides was evaluated. Using the basic procedure for digestion outlined above, it was found that tertiary organophosphines with nucleophilic side chains cleave proteins containing cysteine residues while tertiary organophosphines without nucleophilic side chains act as reducing agents but do not cleave such proteins. For example, tertiary organophosphines with tris-carboxyethyl, tris-n-butyl, tris-isobutyl or tri-cyanoethyl side chains, show no sign of cleaving peptide bonds. The results of such an experiment using BSA and tris(isobutyl)phosphine and depicted in FIG. 2. Only the parent, 66K, protein is seen after the reaction.

The nucleophilic tertiary organophosphines of the present invention selectively cleave proteins containing cysteine residues at the cysteine residue sites. Proteins containing numerous cysteine -cysteine sequences, such as bovine serum albumin, are all readily cleaved by the compounds of this invention. Other proteins with fewer cysteine residues may require application of heat to the digestion reaction to push the reaction to completion. The cleavage reaction of the compounds of this invention occurs over a wide pH range (4–12) and can be adjusted for optimal results by one skilled in the art to which this invention pertains. The reaction can be performed in various approporiate aqueous buffer solutions.

Due to the selectively of the cleavage by the compounds of this invention for cysteine residue sites, these compounds are very useful as a reagents for mapping of protein sequences and protein structural analysis. Such mapping and analysis can be performed using the digestion procedures described above.

Since keratins contain a high percentage of cysteine residues, treatment of keratins with the compounds of this invention will solubilize them. By way of example and not of limitation, feathers, callus tissue, hair and nails can be solubilized by these nucleophilic tertiary organophosphines. Such solubilization can be useful as a dehairing agent prior to tanning of animal hides and as an agent for the removal of ingrown toenails or callus tissue.

The compounds of this invention also may have antibacterial, antiviral and antifungal activity since these compounds cleave cystine containing proteins.

With the current advances in biotechnology including the engineering of specific proteins, the compounds of this invention will be useful as additional, selective tools in the modification of proteins by selective cleavage of protein.

The foregoing specified uses for the compounds of this invention are set forth as examples and are not intended, by their inclusion, to limit the scope of this invention in any way. Other uses for the compounds will be evident to those skilled in the art with the benefit of the disclosure contained herein and such uses shall therefore be within the scope of this invention.

We claim:

1. Tertiary phosphines selected from compounds and formula.

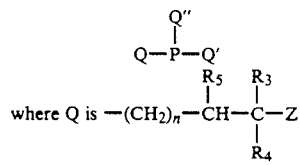

where Q is $-(CH_2)_n-CH-\underset{R_4}{\overset{R_5}{\underset{|}{\overset{|}{C}}}}-Z$

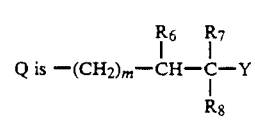

Q' is Q or Q''

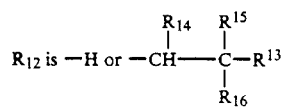

Y and Z are $-NR_{10}R_{11}$ or $-OR_{12}$;

$R_{10}$ and $R_{11}$ taken with the N form imidazolyl, pyrrolidonyl, pyridyl or morpholinyl rings $$R_{12} \text{ is } -H \text{ or } -CH-\underset{R_{16}}{\overset{R_{14}}{\underset{|}{\overset{|}{C}}}}-R^{13}$$ with $R^{15}$ $R_{13}$ is $[CH(R_{17})]_t-OH$ where n,m and t are independently 0–3;

$R_3$, $R_4$, $R_5$, $R_6$, $R_7$, $R_8$, $R_{14}$ and $R_{15}$ are independently H or alkyl ($C_1$–$C_4$);

$R_{16}$—$R_{17}$ are independently —H or OH; with the proviso that Y and Z are not the same for any given compound.

2. The compound 3-N,N-diethylaminopropylbis (3-imidazolylpropyl)phosphine.

3. The compound 3-N,N-diethylaminopropylbis (2-hydroxy-ethyloxy-3-propyl)phosphine.

4. The compound 3-imidazolylpropylbis(3-hydroxypropyl)phosphine.

5. The compound 3-N, N-diethylaminopropylbis(1, 2-dihydroxypropyloxy-3-propyl)phosphine.

6. The compound N-pyrrollidonylethylbis[1,2-dihydroxypropyloxy-3-propyl)phosphine.

7. The compound 3-hydroxypropylbis[3-imidazolypropyl)phosphine.

* * * * *